United States Patent [19]

Faber et al.

[11] Patent Number: 6,133,447
[45] Date of Patent: Oct. 17, 2000

[54] PROCESS FOR THE PREPARATION OF SUBSTITUTED PYRIDINES

[75] Inventors: Dominik Faber, Riehen; Denis Blaser, Choëx; Thierry Bourquard, Delémont; Andrea Rolf Sting, Gipf-Oberfrick, all of Switzerland; Dean Kent Hoglen, Baton Rouge, La.

[73] Assignee: Novartis Crop Protection, Inc., Greensboro, N.C.

[21] Appl. No.: 09/251,549

[22] Filed: Feb. 17, 1999

[30] Foreign Application Priority Data

Feb. 27, 1998 [CH] Switzerland .............................. 0480/98

[51] Int. Cl.$^7$ ...................... C07D 213/61; C07D 213/62; C07D 213/65
[52] U.S. Cl. ............................................. 546/303; 546/345
[58] Field of Search ............................................... 546/303

[56] References Cited

U.S. PATENT DOCUMENTS 4,716,231 12/1987 Goddard ................................... 546/298
5,403,814 4/1995 Fory ........................................ 504/215

FOREIGN PATENT DOCUMENTS 862581 3/1961 United Kingdom .
WO 96/37472 11/1996 WIPO .

OTHER PUBLICATIONS

Ber. Dt. Chem. Ges., vol. 69, No. 12, O.V. Schickh et al., pp. 2593–2605 (1936).
Tetrahedron, 1958, vol. 3, pp. 51–52.
Chem. Abstract 119:183267K (1993).
J. Org. Chem. 49, No. 25, pp. 4784–4786 (1984).
J. Org. Chem. 47, No. 11, pp. 2196–2199 (1982).
Chem. Abst. 31:1808(7) (1937) entitled "Derivatives of 3–aminopyridine" (English language equivalent of Ber. Dt. Chem. Ges., vol. 69, No. 12, O.V. Schickh et al., pp. 2593–2605 (1936).

*Primary Examiner*—Alan L. Rotman
*Attorney, Agent, or Firm*—William A. Teoli, Jr.

[57] ABSTRACT

2-chloro-3-hydroxypyridine is prepared by reacting 3-hydroxypyridine with aqueous sodium hypochlorite.

4 Claims, No Drawings

PROCESS FOR THE PREPARATION OF SUBSTITUTED PYRIDINES

Process for the preparation of substituted pyridines

The present invention relates to a process for the preparation of 2-chloro-3-hydroxypyridine.

2-chloro-3-hydroxypyridine is an important intermediate in the preparation of herbicidally active pyridylsulfonylureas, as are disclosed for example in U.S. Pat No. 5,403,814.

2-chloro-3-hydroxypyridine may be prepared for example by reacting 3-hydroxypyridine with a mixture of boiling hydrochloric acid and hydrogen peroxide. A process of this kind is described in Berichte d. D. Chem. Gesellschaft 69, 2593-2605 (1936). However, the yields achieved with this process, 51% of theory, are unsatisfactory. The improvement in yield to 75% of theory, described in Tetrahedron, 1958, Vol. 3, 51-52, by irradiating with ultraviolet light, cannot be used in particular for large-scale production. It is therefore the object of the present invention to provide a process which enables 2-chloro-3-hydroxypyridine to be prepared in a simple manner and in high yields.

It has now been found that 2-chloro-3-hydroxypyridine can be particularly advantageously prepared in an economical and ecological manner by reacting 3-hydroxypyridine with sodium hypochlorite in an aqueous medium.

3-hydroxypyridine is known and is obtainable e.g. commercially. For example, the preparation of 3-hydroxypyridine in dilute hydrochloric acid is described in GB 862581.

In a preferred embodiment of the process according to the invention, a mixture of 3-hydroxypyridine and sodium hydroxide is reacted with aqueous sodium hypochlorite in an aqueous medium.

Preparation of the mixture of 3-hydroxypyridine and sodium hydroxide in an aqueous medium is effected by adding aqueous sodium hydroxide solution to the 3-hydroxypyridine. This addition may be effected at temperatures of −20 to 100° C., preferably at 0 to 20° C. The reaction of 3-hydroxypyridine and sodium hydroxide with sodium hypochlorite preferably takes place at temperatures of −10 to 100° C., most preferably at −5 to 10° C.

The sodium hydroxide is preferably used in an amount of up to 2 equivalents, most preferably 1 to 1.2 equivalents, based on the 3-hydroxypyridine. The sodium hypochlorite is preferably used in an amount of 0.9 to 2 equivalents, most preferably 1 to 1.1 equivalents, based on the 3-hydroxypyridine.

The concentration of the aqueous sodium hydroxide solution is preferably 30% by weight, and that of the sodium hypochlorite solution is 10 to 15% by weight.

The sodium hypochlorite is introduced at a pH value of 11 to 13, preferably at a pH value of 12. The pH value may be preferably adjusted by simultaneously introducing up to 2 equivalents of aqueous hydrochloric acid until the hypochlorite has completely reacted. An amount of 1.1 to 1.3 equivalents of concentrated aqueous hydrochloric acid is preferred (32 to 37%).

In an especially preferred embodiment of the process according to the invention, when the 3-hydroxypyridine starting product has been produced, it is used without isolation in its hydrochloric-acid-containing reaction medium. In this way, it is particularly advantageous that, in order to adjust the pH value when introducing the sodium hypochlorite, no additional acid has to be used. The amount of undesired by-products of the reaction is thus considerably reduced. In addition, the time-consuming isolation of the 3-hydroxypyridine from its reaction mixture can be dispensed with, which would otherwise lead to losses of yield.

In this embodiment, 2-chloro-3-hydroxypyridine is preferably produced by adding 2-aminomethylfuran and chlorine preferably simultaneously to a solution of water and hydrochloric acid, the pH value being held constant at −1 to 5, preferably at −0.5 to 1, by an aqueous hydroxide, for example potassium hydroxide or sodium hydroxide, preferably sodium hydroxide, subsequently, after cooling and filtering the reaction mixture thus obtained, placing 30 to 60%, preferably 40%, of the total amount of this reaction mixture in a reaction vessel, setting a pH value of 11 to 13, preferably 12, with aqueous sodium hydroxide solution, and after cooling to −5 to 5° C., preferably to 0 to 5° C., adding the remaining amount of the 3-hydroxypyridine reaction mixture and also the aqueous sodium hypochlorite solution, preferably simultaneously.

When the reaction has ended, the pH value is adjusted to 2 to 7, preferably 3 to 4, in order to separate the 2-chloro-3-hydroxypyridine. This pH adjustment is effected by using an aqueous acid at temperatures of 0 to 100° C., preferably 20 to 60° C. The type of acid is not critical, hydrochloric acid, sulphuric acid or phosphoric acid being suitable for example, most preferably hydrochloric acid. The product obtained is subsequently filtered, the residue of filtration being washed preferably with water, most preferably with a mixture of water, sodium chloride and hydrochloric acid (pH 3 to 4) at a temperature of 0 to 25° C.

PREPARATIVE EXAMPLES

Example H1

383 g of a 12% aqueous sodium hypochlorite solution are added dropwise at a temperature of 0° C. over the course of 2 hours to a mixture of 60 g of 3-hydroxypyridine and 99 g of 30% aqueous sodium hydroxide solution. During this time, until the reaction has terminated, the pH value of the reaction mixture is maintained at 12 by adding 82 g of of 37% concentrated hydrochloric acid. To separate the 2-chloro-3-hydroxypyridine from the reaction mixture, the pH value is adjusted to 3 with 68 g of 37% concentrated hydrochloric acid at a temperature of 25° C., the mixture is filtered, washed with aqueous sodium chloride solution and dried in a vacuum. 2-chloro-3-hydroxypyridine is obtained in a yield of 85% of theory.

Example H2

45 g of chlorine and 60 g of 2-aminomethylfuran are added simultaneously, at a temperature of 80° C., to a solution of 140 g of water and 7.5 g of 32% hydrochloric acid, the pH value being held constant at −0.5 to 1 by adding aqueous sodium hydroxide. When the reaction is complete, the reaction mixture is cooled and filtered. 40% of this reaction mixture is then placed in a reaction vessel, the pH value is adjusted to 12 with aqueous sodium hydroxide, and the solution is cooled to a temperature of 0 to 5° C. The remaining 60% of the reaction mixture is added simultaneously with 335 g of 15% aqueous sodium hypochlorite solution at a temperature of 0 to 5° C. When the reaction is complete, the excess NaOCl is broken down with sodium hydrogen sulphite and the mixture is neutralised with hydrochloric acid. After filtering, washing with water and xylene and drying, 65 g (81% of theory) of 2-chloro-3-hydroxypyridine are obtained.

What is claimed is:

1. A process for the preparation of 2-chloro-3-hydroxypyridine, which comprises reacting 3-hydroxypyridine with sodium hypochlorite in an aqueous medium.

2. A process according to claim 1, which comprises using 3-hydroxypyridine in a solution containing hydrochloric acid.

3. A process according to claim 2, which comprises using 3-hydroxypyridine, which is obtained by adding 2-aminomethylfuran and chlorine to a solution of water and hydrochloric acid, whilst maintaining a constant pH value with aqueous hydroxide.

4. A process according to claim 2, which comprises placing 30 to 70% of the total amount of hydrochloric-acid-containing 3-hydroxypyridine solution in a reaction vessel, setting a pH value of 11 to 13 with aqueous sodium hydroxide solution, and after cooling to −5 to 5° C., adding the remaining amount of hydrochloric-acid-containing 3-hydroxypyridine and the aqueous sodium hypochlorite solution simultaneously.

* * * * *